(12) United States Patent
Candau et al.

(10) Patent No.: US 6,403,061 B1
(45) Date of Patent: Jun. 11, 2002

(54) UV-PHOTOPROTECTING W/O EMULSIONS COMPRISING MICRONIZED INSOLUBLE SCREENING AGENTS & NONSCREENING OXYALKYLENATED SILICONES

(75) Inventors: Didier Candau, Bievres; Serge Forestier, Claye Souilly, both of (FR)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 09/693,888

(22) Filed: Oct. 23, 2000

(30) Foreign Application Priority Data

Oct. 22, 1999 (FR) .............................. 98 13219

(51) Int. Cl.$^7$ .............................. A61K 7/42; A61K 7/44; A61K 7/00; A61K 31/53
(52) U.S. Cl. .............................. 424/59; 424/60; 424/400; 424/401; 514/241
(58) Field of Search .............................. 424/59, 60, 400, 424/401; 514/241

(56) References Cited

FOREIGN PATENT DOCUMENTS

FR  2 771 926 A1  6/1999

*Primary Examiner*—Shelly A. Dodson
(74) *Attorney, Agent, or Firm*—Burns, Doane, Swecker & Mathis, L.L.P.

(57) ABSTRACT

Topically applicable, water-resistant cosmetic/dermatological water-in-oil (W/O) emulsions well suited for the UV-photoprotection of human skin and/or hair comprise (a) at least one aqueous phase and (b) at least one fatty phase, (c) an effective UV-photoprotecting amount of at least one micronized organic UV-screening agent insoluble therein, the mean particle size of such micronized particles ranging from 0.01 to 2 $\mu$m, and (d) at least one oxyalkylenated non-UV-screening organomodified silicone.

54 Claims, No Drawings

UV-PHOTOPROTECTING W/O EMULSIONS COMPRISING MICRONIZED INSOLUBLE SCREENING AGENTS & NONSCREENING OXYALKYLENATED SILICONES

CROSS-REFERENCE TO COMPANION APPLICATIONS

Copending applications Ser. No. 09/693,889, Ser. No. 09/693,894 and Ser. No. 09/693,887, each assigned to the assignee hereof, each filed concurrently herewith and each also hereby expressly incorporated by reference.

CROSS-REFERENCE TO PRIORITY APPLICATION

This application claims priority under 35 U.S.C. §119 of FR-99/13219, filed Oct. 22, 1999, hereby expressly incorporated by reference.

BACKGROUND OF THE INVENTION

1. Technical Field of the Invention

The present invention relates to novel water-in-oil (W/O) cosmetic/dermatological emulsions comprising at least one aqueous phase and at least one fatty phase; at least one photoprotective system/agent suited for screening out UV-irradiation, including at least one organic UV-screening agent insoluble in such emulsions, in micronized form or state; and also including at least one nonscreening organomodified silicone.

The present invention also relates to cosmetic/dermatological compositions suited for the photoprotection of the skin or of the hair.

2. Description of the Prior Art

It is known to this art that light radiation of wavelengths of from 280 nm to 400 nm permits tanning of the human epidermis, and that radiation of wavelengths more particularly of from 280 nm to 320 nm, i.e., UV-B radiation, causes erythemas and skin burns which can hinder the development of natural tanning.

For these reasons as well as for aesthetic reasons, there is a constant demand to control this natural tanning such as to thereby control the color of the skin; it is therefore advisable to screen out UV-B radiation.

It is also known to this art that UV-A radiation of wavelengths of from 320 nm to 400 nm, which promotes tanning of the skin, also is capable of causing damage thereto, in particular in the case of a sensitive skin or of a skin continually exposed to solar radiation. UV-A radiation, causes, in particular, loss of elasticity of the skin and the appearance of wrinkles which promotes premature skin aging. UV-A radiation promotes the onset of the erythema reaction or amplifies this reaction in certain individuals and may even be responsible for phototoxic or photoallergic reactions. Thus, for aesthetic and cosmetic reasons such as the preservation of the natural elasticity of the skin for example, an increasing number of individuals seek to control the effect of UV-A radiation on their skin. It is therefore desirable to also screen out UV-A radiation.

A wide variety of cosmetic compositions intended for the photoprotection (UV-A and/or UV-B) of the skin are also known to this art.

These anti-sun or sunscreen compositions are quite often provided in the form of an emulsion, of the oil-in-water (O/W) type (namely, a cosmetically and/or dermatologically acceptable carrier comprising an aqueous dispersing continuous phase and a fatty dispersed discontinuous phase) or of the water-in-oil (W/O) type (dispersed aqueous phase in a continuous fatty phase), which contains, at various concentrations, one or more lipophilic conventional organic UV-screening agents and/or inorganic nanopigments of metal oxides, which are suited for selectively absorbing the harmful UV radiation, these screening agents (and the quantities thereof) being selected according to the desired sun protection factor (the sun protection factor (SPF) being mathematically expressed by the ratio of the irradiation time required to attain the erythematogenic threshold with the UV-screening agent to the time required to attain the erythematogenic threshold in the absence of UV-screening agent). In such emulsions, the hydrophilic screening agents are present in the aqueous phase and the lipophilic screening agents are present in the fatty phase.

The oil-in-water emulsions are, in general, more accepted by the consumer than the water-in-oil emulsions because, in particular, of their pleasant feel (similar to water) and their presentation in the form of a non-oily cream or milk; however, they also more readily lose their UV protection efficacy as soon as they come into contact with water. Indeed, the hydrophilic screening agents tend to disappear in water, upon washing in the sea or in a swimming pool, under the shower or when engaged in water sports; thus, anti-sun or sunscreen compositions containing same, whether alone or combined with lipophilic screening agents, no longer provide the desired initial protection as soon as the substrate (skin or hair) to which they have been applied is contacted with water.

Anti-sun (sunscreen) compositions exhibiting improved resistance to water have been formulated as water-in-oil emulsions. Indeed, a hydrophilic screening agent is more stable to water in a water-in-oil emulsion than in an oil-in-water emulsion. However, as indicated above, such compositions are not yet completely satisfactory since they promote, after application, a fat-like impression which is particularly unpleasant for the user.

Thus, serious need continues to exist for anti-sun or sunscreen compositions which impart to the skin and/or the hair effective solar protection which is stable over time and resistant to water (stability to water) and the cosmetic performance of which presents features that would be comparable to those obtained with conventional oil/water emulsions.

SUMMARY OF THE INVENTION

It has now surprisingly and unexpectedly been determined that specific emulsions containing at least one organic UV-screening agent insoluble in micronized form in the different phases of these emulsions and at least one particular non-UV-screening organomodified silicone not only provide anti-sun compositions whose cosmetic performance features are comparable to those generally associated with a conventional sunscreen composition formulated as an oil/water or water/oil emulsion, but also exhibit good stability as well as enhanced stability to water.

These discoveries constitute the basis of the present invention.

Briefly, the present invention features cosmetic/dermatological water-in-oil emulsions comprising:

(a) at least one aqueous phase and
(b) at least one fatty phase;
(c) at least one photoprotective system or agent suited for screening out UV radiation, containing at least one organic UV-screening agent insoluble in such emulsions, in micronized form, in which the mean size of the particles ranges from 0.01 to 2 μm;

(d) at least one non-UV-screening organomodified silicone which comprises oxyalkylenated substituents. Characteristically, said organic UV-screening agent is neither 2,4,6-tris[p-(2'-ethylhexyl-1'-oxycarbonyl)anilino]-1,3,5-triazine in micronized insoluble form nor the compound having the structural formula:

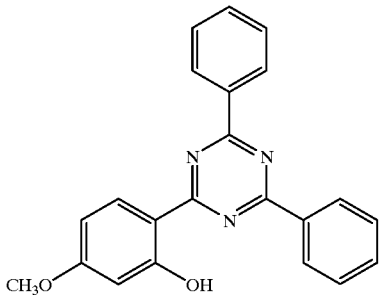

in micronized insoluble form.

DETAILED DESCRIPTION OF BEST MODE AND SPECIFIC/PREFERRED EMBODIMENTS OF THE INVENTION

More particularly according to the present invention, by "cosmetic or dermatological emulsion" is intended any emulsion in which the aqueous phase and the fatty phase contain substances or substrates which are cosmetically or dermatologically acceptable for topical application onto human keratinous materials including the skin, the hair, the eyelashes, the eyebrows, the lips, the nails or the mucous membranes.

By "non-screening silicone" is intended any silicone not containing in its structure a functional group which absorbs UV radiation.

By "insoluble organic UV-screening agent" is intended according to the present invention organic UV-screening agents which are insoluble in the cosmetic media generally included in anti-sun formulations and more particularly whose solubility in water at 25° C. is less than 0.1% by weight and whose solubility in paraffin oil at 25° C. is less than 1% by weight.

By "photoprotective system suited for screening out UV radiation" is intended any system including one or more organic compounds and/or inorganic compounds screening out UV-A and/or UV-B radiation.

The present invention thus features formulating the subject emulsions into cosmetic compositions for the protection of the skin and/or of the hair against ultraviolet radiation, in particular solar radiation.

The present invention also features formulating non-UV-screening organomodified silicones containing oxyalkylenated functional groups into photoprotective cosmetic/dermatological emulsions containing at least one organic UV-screening agent insoluble in the emulsion, in micronized form or state, the mean particle size of which ranges from 0.01 to 2 μm, to increase or enhance the water resistance of their screening power (stability to water).

As is generally accepted, by "silicone" is intended any organosilicon polymer or oligomer having a linear or cyclic, branched or crosslinked structure, of variable molecular weight, prepared via polymerization and/or polycondensation of appropriately functionalized silanes, and essentially consisting of recurring structural units in which the silicon atoms are linked to each other by oxygen atoms (siloxane bond (SiOSi)), optionally substituted hydrocarbon radicals being directly linked via a carbon atom to the silicon atoms. The most common hydrocarbon radicals are alkyl, especially $C_1$–$C_{10}$ and in particular methyl, radicals, fluoroalkyl radicals, aryl, and in particular phenyl, radicals. The silicones are described in greater detail in the text by Walter NOLL *Chemistry and Technology of Silicones*, Academic Press (1968).

The organomodified silicones according to the invention are silicones as described above and comprising, in their structure, one or more organofunctional groups attached via a hydrocarbon radical. The silicones according to the invention may be provided in the form of oils, waxes, resins or gums. They may be water-soluble or insoluble in water.

Particularly exemplary non-UV-screening silicones comprising oxyalkylenated (in particular oxyethylenated and/or oxypropylenated) functional groups are those having the following structural formula (I):

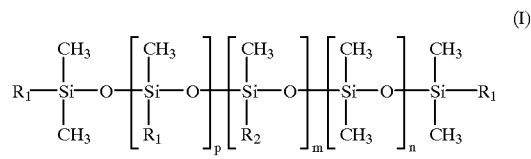

(I)

in which the radicals $R_1$, which may be identical or different, are each a linear or branched $C_1$–$C_{30}$ alkyl radical or a phenyl radical; the radicals $R_2$, which may be identical or different, are each a —$C_cH_{2c}$(—O—$C_2H_4$)$_a$—(—O—$C_3H_6$)$_b$—(O—$C_4H_8$)$_d$—$R_3$ radical; the radicals $R_3$, which may be identical or different, are each a hydrogen atom, a hydroxyl radical, a linear or branched alkyl radical having from 1 to 12 carbon atoms, a linear or branched alkoxy radical having from 1 to 6 carbon atoms, a linear or branched acyloxy radical having from 2 to 12 carbon atoms, a radical —NHCH$_2$CH$_2$COOM, an aminoalkyl radical optionally substituted on the amine function, a $C_1$–$C_{30}$ carboxyacyl radical, an optionally substituted phosphono group, or a radical —O—CO—(CH$_2$)$_d$—CO$_2$M, —NHCO(CH$_2$)$_d$OH or —NH$_3$Y, wherein M is a hydrogen atom, Na, K, Li, NH$_4$ or an organic amine, and Y is a monovalent inorganic or organic anion, such as halide (chloride, bromide), sulfate, carboxylate (acetate, lactate, citrate); a ranges from 0 to 100; b ranges from 0 to 50; c ranges from 0 to 5; a+b is greater than or equal to 1; d ranges from 0 to 10; m ranges from 1 to 20; n ranges from 0 to 500; p ranges from 0 to 50.

Representative silicones according to the invention include those marketed under the trademarks FLUID DC 193 by Dow Corning, SILWET L 77 by OSI and MAZIL 756 by MAZER PPG; also representative are the silicones marketed under the trademarks "Silicone DC 3225C" "DC Q2-5200" by Dow Corning.

Herein, EO represents one mol of ethylene oxide and PO represents one mol of propylene oxide.

A particular first family of non-UV-screening silicones comprising oxyalkylenated substituents especially suitable for the emulsions of the invention is that corresponding to the above formula (I) in which the radicals $R_1$ are all methyl radicals and the radical $R_3$ is a hydroxyl radical.

An exemplary silicone emulsifier belonging to this family is oxyethylenated oxypropylenated polydimethyl/methyl siloxane (EO/PO 18/18) for which p+n is 396 and m is 4, (CTFA name: cyclomethicone 90% dimethicone copolyol 10%) marketed under the trademark "Silicone Q2-3225C" by Dow Corning.

A second family of non-UV-screening silicones comprising oxyalkylenated substituents particularly suitable for the emulsions of the invention is that corresponding to the above formula (I) in which the radicals $R_1$ are methyl radicals and lauryl radicals and the radical $R_3$ is a hydroxyl radical.

A particularly preferred silicone emulsifier of this second family is oxyethylenated oxypropylenated polymethyllauryl/methyl siloxane (EO/PO 18/18) for which p+n is 35 and m is 3 (CTFA name: laurylmethicone copolyol 91%, isostearyl alcohol 8%) marketed under the trademark "DC Q2-5200" by Dow Corning.

Another particularly preferred silicone emulsifier of this second family is oxyethylenated oxypropylenated polymethylcetyl/methyl siloxane, for which p is 20 to 25 and m is 5 and n is 75 (CTFA name: cetyldimethicone copolyol) marketed under the trademark "Abil EM 90" by Goldschmidt.

A silicone emulsifier which is most particularly preferred for the emulsions according to the invention is an α,ω-substituted oxyalkylenated silicone having a linear structure, substituted at the two ends of the principal chain with oxyalkylene groups linked to the Si atoms via a hydrocarbon group. More particularly, the preferred silicones have the following general formula (II):

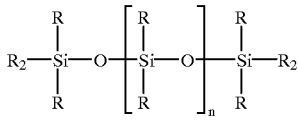

(II)

in which n ranges from 1 to 500; the radicals $R_2$, which may be identical or different, are each a radical $-C_cH_{2c}-(-O-C_2H_4)_a-(-O-C_3H_6)_b-(-O-C_4H_8)_d-R_3$ wherein a, b, c and $R_3$ are as defined above in formula (I) and the radicals R, which may be identical or different, are each a linear or branched $C_1-C_{30}$ alkyl radical.

More preferably, all of the radicals R are methyl radicals; c ranges from 2 to 4, a ranges from 3 to 100, b ranges from 1 to 50, d equals 0, $R_3$ is a hydroxyl radical, and n ranges from 50 to 200.

Preferably, the weight ratio of the $C_2H_4O$ units relative to the $C_3H_6O$ units ranges from 100:10 to 20:80. Advantageously, this ratio is about 58/42.

Among the commercial products which may contain all or some of the α,ω-substituted oxyalkylenated silicones according to the invention as emulsifier, particularly exemplary are those marketed under the trademarks "Abil EM 97" by Goldschmidt, or "KF 6009", "X22-4350", "X22-4349" or "KF 6008" by Shin Etsu.

The non-UV-screening organomodified silicone(s) according to the present invention are preferably formulated in concentrations ranging from 0.1% to 20% relative to the total weight of the composition, and more particularly in an amount ranging from 0.5% to 10%.

The insoluble organic UV-screening agents in accordance with this invention may be selected, in particular, from among the organic UV-screening agents of the oxanilide type, of the triazine type, of the triazole type, of the vinylamide type and of the cinnamide type.

Exemplary UV-screening agents of the oxanilide type include those having the structural formula (1):

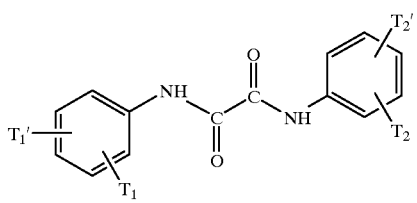

(1)

in which $T_1$, $T'_1$, $T_2$ and $T'_2$, which may be identical or different, are each a $C_1-C_8$ alkyl radical or a $C_1-C_8$ alkoxy radical. These compounds are described in WO-95/22,959.

Exemplary thereof are the commercial products TINUVIN 315 and TINUVIN 312 marketed by Ciba-Geigy and respectively having the structural formulae:

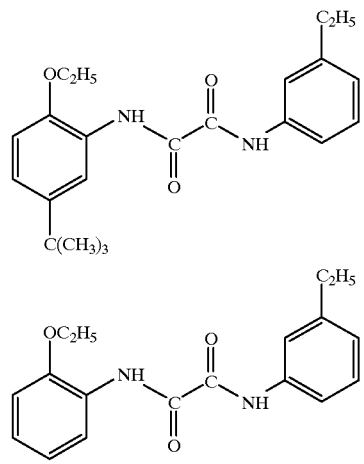

The preferred 1,3,5-triazine derivatives in accordance with the invention have the following structural formula (2):

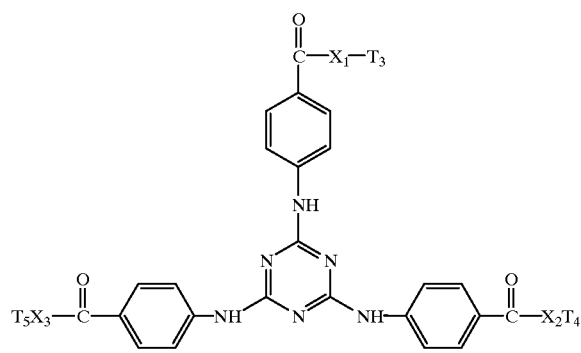

(2)

in which $X_1$, $X_2$ and $X_3$, which may be identical or different, are each an oxygen atom or a radical $-NZ-$; the radicals Z, which may be identical or different, are each hydrogen or a linear or branched $C_1-C_{18}$ alkyl radical, a $C_5-C_{12}$ cycloalkyl radical optionally substituted with one or more $C_1-C_4$ alkyl radicals; $T_3$, $T_4$ and $T_5$, which may be identical or different, are each hydrogen, an alkali metal, an ammonium radical which is optionally substituted with one or more alkyl or hydroxyalkyl radicals, a linear or branched $C_1-C_{18}$ alkyl radical, a $C_5-C_{12}$ cycloalkyl radical which is optionally substituted with one or more $C_1-C_4$ alkyl radicals, a polyoxyethylenated radical having from 1 to 6 ethylene oxide units and whose terminal OH group is methylated or a radical of the following formulae (3), (4) or (5):

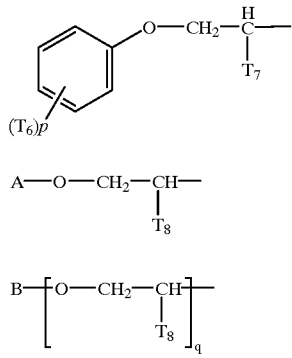

(3)

$$A\text{---}O\text{---}CH_2\text{---}CH\text{---}$$
$$\hspace{2em}|$$
$$\hspace{2em}T_8$$

(4)

$$B\text{---}\!\left[O\text{---}CH_2\text{---}CH\right]\!_q\text{---}$$
$$\hspace{4em}|$$
$$\hspace{4em}T_8$$

(5)

in which $T_6$ is hydrogen or a methyl radical; $T_7$ is a $C_1$–$C_9$ alkyl radical; p is an integer ranging from 0 to 3; q is an integer ranging from 1 to 10; A is a $C_4$–$C_8$ alkyl radical or a $C_5$–$C_8$ cycloalkyl radical; B is a linear or branched $C_1$–$C_8$ alkyl radical, a $C_5$–$C_8$ cycloalkyl radical, an aryl radical which is optionally substituted with one or more $C_1$–$C_4$ alkyl radicals; and $T_8$ is hydrogen or a methyl radical.

A first preferred family of 1,3,5-triazine derivatives is that which is, in particular, described in EP-A-0,517,104 (expressly incorporated by reference herein), and the 1,3,5-triazines having the above formula (2) while satisfying all of the following characteristics:

(i) $X_1$, $X_2$ and $X_3$ are identical and are each an oxygen atom;

(ii) $T_3$ is a $C_5$–$C_{12}$ cycloalkyl radical which is optionally substituted with one or more $C_1$–$C_4$ alkyl radicals, a radical of formula (3), (4) or (5) above in which B is a $C_1$–$C_4$ alkyl radical, and $T_8$ is the methyl radical;

(iii) $T_4$ and $T_5$, which may be identical or different, are each hydrogen, an alkali metal, an ammonium radical which is optionally substituted with one or more alkyl or hydroxyalkyl radicals, a linear or branched $C_1$–$C_{18}$ alkyl radical, a $C_5$–$C_{12}$ cycloalkyl radical which is optionally substituted with one or more $C_1$–$C_4$ alkyl radicals, or a radical of formula (3), (4) or (5) above in which B is a $C_1$–$C_4$ alkyl radical and $T_8$ is a methyl radical.

A second preferred family of 1,3,5-triazine derivatives according to the invention is that, in particular, described in EP-A-0,570,838 (also hereby expressly incorporated by reference), and the 1,3,5-triazines having the formula (2) and satisfying all of the following characteristics:

(i) $X_1$ is an oxygen atom, $X_2$ is the —NH— radical or an oxygen atom, and $X_3$ is the —NH— radical;

(ii) $T_5$ is a linear or branched $C_1$–$C_{18}$ alkyl radical, or a $C_5$–$C_{12}$ cycloalkyl radical which is optionally substituted with one or more $C_1$–$C_4$ alkyl radicals;

(ii) $T_3$ is hydrogen, an alkali metal, an ammonium radical, a radical of formula (5), a linear or branched $C_1$–$C_{18}$ alkyl radical, a $C_5$–$C_{12}$ cycloalkyl radical which is optionally substituted with one or more $C_1$–$C_4$ alkyl radicals, with the proviso that if $X_2$ is the —NH— radical, then $T_4$ is a linear or branched $C_1$–$C_{18}$ alkyl radical, or a $C_5$–$C_{12}$ cycloalkyl radical which is optionally substituted with one or more $C_1$–$C_4$ alkyl radicals;

and with the further proviso that if $X_2$ is an oxygen atom, then $T_4$ is hydrogen, an alkali metal, an ammonium radical, a radical of formula (5), a linear or branched $C_1$–$C_{18}$ alkyl radical, or a $C_5$–$C_{12}$ cycloalkyl radical which is optionally substituted with one or more $C_1$–$C_4$ alkyl radicals.

A third preferred family of 1,3,5-triazine derivatives according to the invention is that, in particular, described in EP-A-0,796,851 (also expressly incorporated by reference), and the 1,3,5-triazines having the formula (2) and satisfying all of the following characteristics:

(i) $X_1$, $X_2$ and $X_3$ are each —NZ—;

(ii) the radicals Z, which may be identical or different, are each hydrogen or a linear or branched $C_1$–$C_{18}$ alkyl radical, or a $C_5$–$C_{12}$ cycloalkyl radical which may be substituted with one or more $C_1$–$C_4$ alkyl radicals;

(iii) $T_3$, $T_4$ and $T_5$, which may be identical or different, are each hydrogen or a radical Z.

These organic UV-screening agents of the triazine type are described in U.S. Pat. No. 4,617,390 and in EP-0,517,104, EP-0,570,838 and EP-0,796,851 (expressly incorporated by reference).

Exemplary UV-screening agents of the triazine type of formula (2) are, more particularly:

2,4,6-tris[p-(2'-ethylhexyl-1'-oxycarbonyl)anilino]-1,3,5-triazine which is a screening agent known per se, active in the UV-B range, existing in solid form, and which is marketed, in particular, under the trademark "UVINUL T150" by BASF this product has the following structural formula:

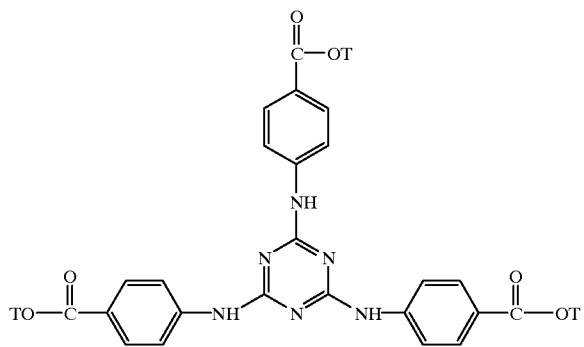

in which T is a 2-ethylhexyl radical; and

2-[(p-(tert-butylamido)anilino]-4,6-bis[(p-(2'-ethylhexyl-1'-oxycarbonyl)anilino]-1,3,5-triazine, having the following structural formula:

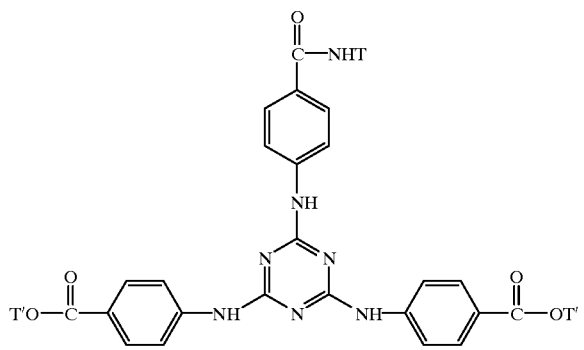

in which T' is a 2-ethylhexyl radical and T is a tert-butyl radical.

Also exemplary insoluble UV-screening agents of the triazine type in accordance with the invention are the insoluble derivatives of s-triazine substituted by benzalmalonate and/or phenylcyanoacrylate groups, such as those described in EP-A-0,790,243 (also expressly incorporated by reference).

Among these UV-screening agents of the triazine type, the following compounds are more particularly exemplary:

2,4,6-tris(diethyl 4'-aminobenzalmalonate)-s-triazine;

2,4,6-tris(diisopropyl 4'-aminobenzalmalonate)-s-triazine;

2,4,6-tris(dimethyl 4'-aminobenzalmalonate)-s-triazine;

2,4,6-tris(ethyl α-cyano-4-aminocinnamate)-s-triazine.

Among the insoluble UV-screening agents of the triazine type in accordance with the invention are those having the following structural formula (6):

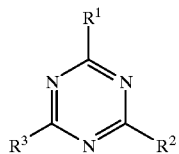

(6)

in which $R^1$, $R^2$, $R^3$ are independently phenyl, phenoxy, pyrrolo, in which the phenyl, phenoxy and pyrrolo radicals are optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a methylidenecamphor group, a group —(CH=CH)$_n$(CO)—OR$^4$, wherein $R^4$ is either $C_1$–$C_{18}$ alkyl or cinnamyl, and n is equal to 0 or 1.

These compounds are described in WO-97/03,642, GB-2,286,774, EP-0-743,309, WO-98/22,447, GB-2,319,523 (expressly incorporated by reference).

Among the insoluble UV-screening agents of the triazine type in accordance with the invention, exemplary are the insoluble derivatives of s-triazine substituted by benzotriazole and/or benzothiazole groups, such as those described in WO-98/25,922 (also expressly incorporated by reference).

More particularly exemplary are:

2,4,6-tris[(3'-benzotriazol-2-yl-2'-hydroxy-5'-methyl)phenylamino]-s-triazine; and 2,4,6-tris[(3'-benzotriazol-2-yl-2'-hydroxy-5'-ter-octyl)phenylamino]-s-triazine.

Exemplary organic UV-screening agents of the triazole type in accordance with the invention are those of the following structural formula (7) as described in WO-95/22,959 (also expressly incorporated by reference):

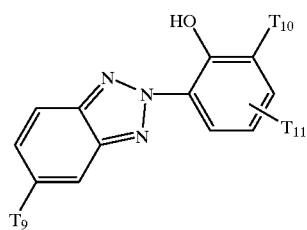

(7)

in which $T_9$ is a hydrogen atom or a $C_1$–$C_{18}$ alkyl radical; and $T_{10}$ and $T_{11}$, which may be identical or different, are each a $C_1$–$C_{18}$ alkyl radical which is optionally substituted with a phenyl radical.

Exemplary compounds of formula (7) are the commercial products TINUVIN 328, 320, 234 and 350 marketed by Ciba-Geigy having the following structural formulae:

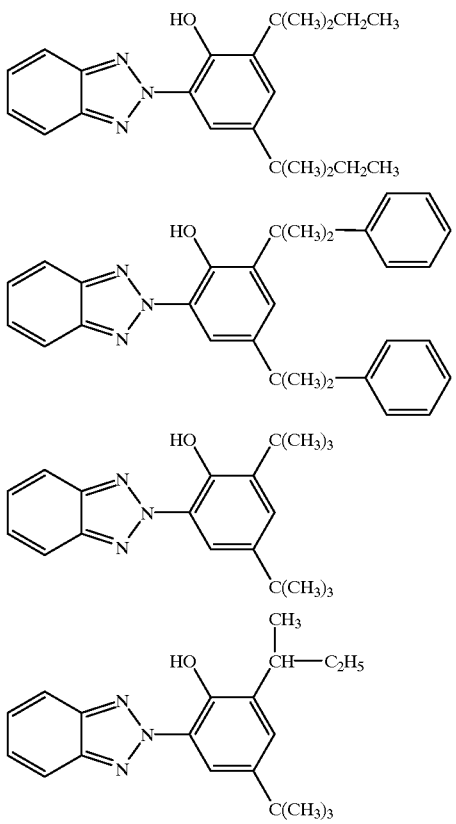

Exemplary organic UV-screening agents of the triazole type in accordance with the invention are the compounds described in U.S. Pat. Nos. 5,687,521, 5,687,521, 5,373,037, 5,362,881 and, in particular, [2,4'-dihydroxy-3-(2H-benzotriazol-2-yl)-5-(1,1,3,3-tetramethylbutyl)-2'-n-octoxy-5'-3-(2H-benzotriazol-2-yl)-5-(1,1,3,3-tetramethylbutyl)-2'-n-octoxy-5'-benzoyl]diphenylmethane marketed under the trademark MIXXIM PB30 by Fairmount Chemical and having the structural formula:

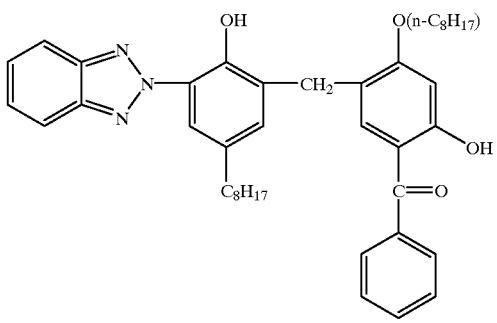

And exemplary organic UV-screening agents of the benzotriazole type in accordance with the invention are the methylenebis(hydroxyphenyl-benzotriazole) compounds having the following structural formula:

(8)

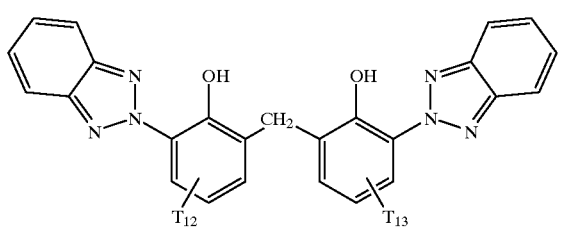

in which the radicals $T_{12}$ and $T_{13}$, which may be identical or different, are each a $C_1$–$C_{18}$ alkyl radical which may be substituted with one or more radicals selected from among a $C_1$–$C_4$ alkyl, a $C_5$–$C_{12}$ cycloalkyl, or an aryl radical. These compounds are per se known and are described in U.S. Pat. Nos. 5,237,071 and 5,166,355, GB-A-2,303,549, DE-197, 26,184 and EP-A-893,119 (also expressly incorporated by reference).

In formula (8) above, the $C_1$–$C_{18}$ alkyl radicals may be linear or branched and include, for example, methyl, ethyl, n-propyl, isopropyl, n-butyl, isobutyl, tert-butyl, tert-octyl, n-amyl, n-hexyl, n-heptyl, n-octyl, iso-octyl, n-nonyl, n-decyl, n-undecyl, n-dodecyl, tetradecyl, hexyldecyl or octadecyl; the $C_5$–$C_{12}$ cycloalkyl radicals include, for example, cyclopentyl, cyclohexyl, cyclooctyl; and the aryl radicals include, for example, phenyl or benzyl.

Among the compounds of formula (8), those having the following structural formula are particularly preferred:

compound (a)

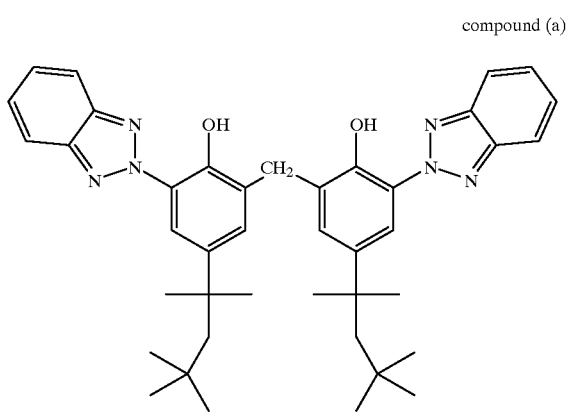

compound (b)

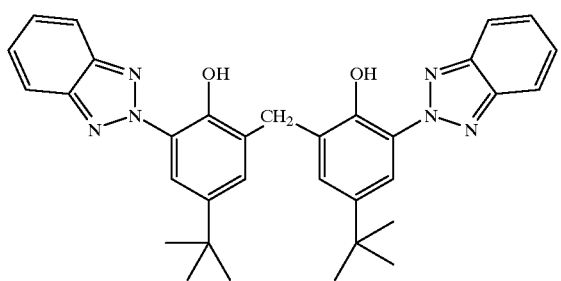

compound (c)

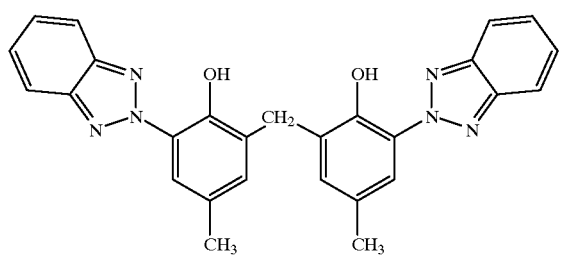

The compound (a) with the nomenclature 2,2'-methylenebis[6-(2H-benzotriazol-2-yl)-4-(1,1,3,3-tetramethylbutyl)phenol] is marketed under the trademark MIXXIM BB/100 by Fairmount Chemical. It is marketed in micronized form under the trademark TINOSORB M by Ciba-Geigy.

The compound (c) with the nomenclature 2,2'-methylenebis[6-(2H-benzotriazol-2-yl)-4-(methyl)phenol] is marketed under the trademark MIXXIM BB/200 by Fairmount Chemical.

Among the organic screening agents of the vinylamide type in accordance with the invention, exemplary are the compounds of the following formulae which are described in WO-95/22,959 (expressly incorporated by reference):

$$T_{14}-(Y)r-C(=O)-C(T_{15})=C(T_{16})-N(T_{17})(T_{18}) \qquad (9)$$

in which $T_{14}$ is a $C_1$–$C_{18}$, preferably $C_1$–$C_5$, alkyl radical or a phenyl group which is optionally substituted with one, two or three radicals selected from among OH, $C_1$–$C_{18}$ alkyl, $C_1$–$C_8$ alkoxy, or a radical —C(=O)—OT$_{19}$ wherein $T_{19}$ is a $C_1$–$C_{18}$ alkyl radical; $T_{15}$, $T_{16}$, $T_{17}$ and $T_{18}$, which may be identical or different, are each a $C_1$–$C_{18}$, preferably $C_1$–$C_5$, alkyl radical or a hydrogen atom; Y is N or O and r is equal to 0 or 1.

Among these compounds, particularly representative are:
4-octylamino-3-penten-2-one;
ethyl 3-octylamino-2-butenoate;
3-octylamino-1-phenyl-2-buten-1-one;
3-dodecylamino-1-phenyl-2-buten-1-one.

Exemplary insoluble organic screening agents of the cinnamamide type are those compounds described in WO-95/22,959 (expressly incorporated by reference) and having the following structural formula:

(10)

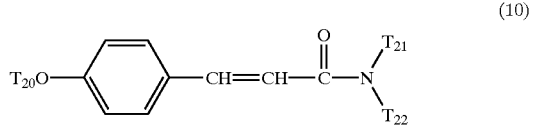

in which $T_{20}$ is a hydroxyl or $C_1$–$C_4$ alkoxy, preferably methoxy or ethoxy, radical; $T_{21}$ is hydrogen, $C_1$–$C_4$ alkyl, preferably methyl or ethyl; $T_{22}$ is a radical —(CONH)s-phenyl wherein s is equal to 0 or 1 and the phenyl group may be substituted with one, two or three groups selected from among OH, $C_1$–$C_{18}$ alkyl, $C_1$–$C_8$ alkoxy, or a radical —C(=O)—OT$_{23}$ wherein $T_{23}$ is a $C_1$–$C_{18}$ alkyl and more preferably $T_{23}$ is a phenyl, 4-methoxyphenyl or phenylaminocarbonyl group.

Also exemplary are the cinnamamide dimers such as those described in U.S. Pat. No. 5,888,481, for example, the compound having the structural formula:

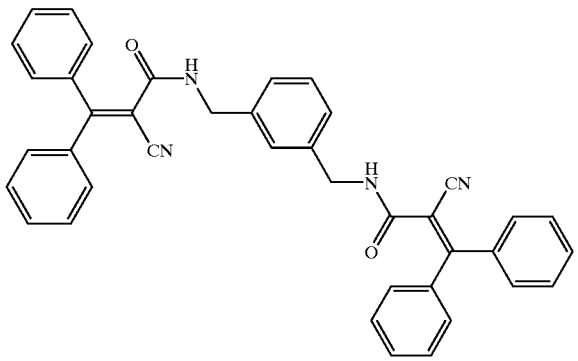

Another specific family of insoluble organic UV-screening agents in accordance with the invention are the polyvalent metal salts (for example $Ca^{2+}$, $Zn^{2+}$, $Mg^{2+}$, $Ba^{2+}$, $Al^{3+}$ or $Zr^{4+}$) of sulfonic or carboxylic organic screening agents such as the polyvalent metal salts of sulfonated derivatives of benzylidenecamphor, for example those described in FR-A-2,639,347; the polyvalent metal salts of sulfonated derivatives of benzimidazole, for example those described in EP-A-893,119; and the polyvalent metal salts of cinnamic acid derivatives, for example those described in JP-87/166,517.

Also representative are the metal or ammonium or substituted ammonium complexes of organic UV-A and/or UV-B screening agents as described in WO-93/10,753, WO-93/11,095 and WO-95/05,150.

The micronized insoluble organic screening agent(s) according to the invention are generally present in the screening compositions according to the invention at a total concentration ranging from 0.1% and 15% by weight approximately, and preferably from 0.2% and 10% by weight approximately, relative to the total weight of the composition.

The insoluble organic screening agents according to the invention are provided in micronized form. The mean or average size of the particles ranges from 0.01 μm to 2 μm and more preferably from 0.02 μm to 1.5 μm and even more preferably from 0.03 μm to 1.0 μm.

The insoluble organic screening agents according to the invention may be provided in the desired particulate form by any appropriate means such as, in particular, grinding in the dry state or in solvent medium, sieving, spray-drying, micronization or spraying.

The insoluble organic screening agents according to the invention in micronized form may, in particular, be provided by a method of grinding an insoluble UV-screening agent in the form of particles having a coarse size in the presence of an appropriate surfactant which makes it possible to enhance the dispersion of the particles thus obtained in the cosmetic formulations.

One embodiment of a method of micronization of insoluble organic screening agents is described in GB-A-2, 303,549 and EP-A-893119 incorporated by reference herein. The grinding apparatus according to the invention may be a jet mill, a ball mill, a vibratory mill or a hammer mill and preferably a mill featuring high-speed agitation or an impact mill and more particularly a rotating ball mill, a vibratory mill, a tube mill or a rod mill.

According to this particular methodology, the alkyl polyglucosides having the structure $C_nH_{2n+1}O(C_6H_{10}O_5)_xH$ in which n is an integer from 8 to 16 and x is the average degree of polymerization of the structural unit $(C_6H_{10}O_5)$ and ranges from 1.4 to 1.6, are included as surfactants for the grinding of the screening agents. They are advantageously selected from among $C_1$–$C_{12}$ esters of a compound having the structure $C_nH_{2n+1}O(C_6H_{10}O_5)_xH$ and more precisely an ester prepared by reacting a $C_1$–$C_{12}$ carboxylic acid such as formic, acetic, propionic, butyric, sulfosuccinic, citric or tartaric acid with one or more free OH functions on the glucoside unit $(C_6H_{10}O_5)$. Such surfactants are typically employed at a concentration ranging from 1% to 50% by weight and more preferably from 5% to 40% by weight relative to the insoluble screening agent in its micronized form.

This invention also features cosmetic or dermatological compositions comprising at least one emulsion as described above.

The anti-sun cosmetic compositions according to the invention may of course contain one or more additional organic screening agents which are active in UV-A and/or UV-B ranges (absorbers), which are soluble in at least one of the phases of the subject compositions. These additional screening agents may be selected, in particular, from among the cinnamic derivatives; the dibenzoylmethane derivatives; the salicylic derivatives, the camphor derivatives; the triazine derivatives such as those described in U.S. Pat. No. 4,367,390, EP-0,863,145, EP-0,517,104, EP-0,570,838, EP-0,796,851, EP-0,775,698, EP-0,878,469 and EP-0,933, 376; the benzophenone derivatives; the dimers derived from α-alkylstyrene such as those described in DE-198,55,649; the β,β'-diphenylacrylate derivatives; the benzimidazole derivatives; the bisbenzoazolyl derivatives as described in EP-A-0,669,323 and U.S. Pat. No. 2,463,264; the p-aminobenzoic acid derivatives; the polymer screening agents and silicone screening agents such as those described, in particular, in WO-93/04,665.

Exemplary such additional sunscreening agents active in the UV-A and/or UV-B ranges, which are soluble in at least one of the phases of the subject compositions, include:

p-aminobenzoic acid;

oxyethylenated p-aminobenzoate (25 mol);

2-ethylhexyl p-dimethylaminobenzoate;

N-oxypropylenated ethyl p-aminobenzoate;

glyceryl p-aminobenzoate;

homomenthyl salicylate;

2-ethylhexyl salicylate;

triethanolamine salicylate;

4-isopropylbenzyl salicylate;

4-tert-butyl-4'-methoxydibenzoylmethane;

4-isopropyl-dibenzoylmethane;

2-ethylhexyl 4-methoxycinnamate;

methyl diisopropylcinnamate;

isoamyl 4-methoxycinnamate;

diethanolamine 4-methoxycinnamate;

menthyl anthranilate;

2-ethylhexyl-2-cyano-3,3'diphenylacrylate;

ethyl 2-cyano-3,3'-diphenylacrylate;

2-phenylbenzimidazole-5-sulfonic acid and salts thereof;

3-(4'-trimethylammonium)benzylidenebornan-2-one methyl sulfate;

2-hydroxy-4-methoxybenzophenone;

2-hydroxy-4-methoxybenzophenone-5-sulfonate;

2,4-dihydroxybenzophenone;

2,2'-4,4'-tetrahydroxybenzophenone;

2,2'-dihydroxy-4,4'-dimethoxybenzophenone;

2-hydroxy-4-n-octoxybenzophenone;

2-hydroxy-4-methoxy-4'-methylbenzophenone;

a-(2-oxoborn-3-ylidene)tolyl-4-sulfonic acid and its soluble salts;

3-(4'-sulfo)benzylidenebornan-2-one and its soluble salts;

3-(4'-methylbenzylidene)-d,1-camphor;

3-benzylidene-d,1-camphor;

1,4-benzene[di(3-methylidene-10-camphorsulfonic)] acid and its soluble salts;

urocanic acid;

2,4-bis{[4-2-ethylhexyloxy)]-2-hydroxy]phenyl}-6-(4-methoxyphenyl)-1,3,5-triazine;

the polymer of N-(2- and 4)-[(2-oxoborn-3-ylidene) methyl]benzyl]acrylamide;

1,4-bisbenzimidazolylphenylene-3,3',5,5'-tetrasulfonic acid and its soluble salts;

polyorganosiloxanes containing a benzalmalonate function;

polyorganosiloxanes containing a benzotriazole function such as Drometrizole Trisiloxane.

The compositions according to the invention may also contain agents for tanning and/or for artificial tanning of the skin (self-tanning agents), such as, for example, dihydroxyacetone (DHA).

The cosmetic compositions according to the invention may also contain pigments or, alternatively, nanopigments (mean size of the primary particles: generally ranging from 5 nm to 100 nm, preferably from 10 nm to 50 nm) of metal oxides, coated or uncoated, such as, for example, nanopigments of titanium dioxide (amorphous or crystallized in the rutile and/or anatase state), of iron oxide, zinc oxide, zirconium oxide or cerium oxide, which are all UV photoprotective agents well known per se. Conventional coating agents are moreover alumina and/or aluminum stearate. Such nanopigments of metal oxides, coated or uncoated, are, in particular, described in EP-A-0,518,772 and EP-A-0,518,773.

The compositions of the invention may comprise, in addition, conventional cosmetic additives and adjuvants selected, in particular, from among fatty substances, organic solvents, thickeners, demulcents, opacifiers, colorants, stabilizers, emollients, antifoaming agents, moisturizing agents, perfumes, preservatives, polymers, fillers, sequestrants, propellants, alkalinizing or acidifying agents or any other ingredient customarily formulated into cosmetics, in particular for the production of anti-sun/sunscreen compositions in the form of emulsions.

The fatty substances may be an oil or a wax or mixtures thereof, and they also comprise fatty acids, fatty alcohols and esters of fatty acids. The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents include the lower alcohols and polyols.

Of course, one skilled in this art will take care to select this or these optional additional compounds and/or their quantities such that the advantageous properties, in particular the resistance to water, the stability, which are intrinsically associated with the emulsions in accordance with the invention are not, or not substantially, altered by the addition (s) envisaged.

The compositions of the invention may be formulated according to techniques well known to this art, in particular those suited for the preparation of emulsions of the water-in-oil type.

The subject compositions may be provided, in particular, in the form of a simple or complex (O/W/O or W/O/W) emulsion such as a cream, a milk, a gel or a gel cream, of a powder, a lotion, an ointment, a solid stick and may optionally be packaged as an aerosol and provided in the form of a foam, mousse or spray.

When an emulsion is provided, the aqueous phase thereof may comprise a nonionic vesicular dispersion prepared according to known techniques (Bangham, Standish and Watkins, *J. Mol. Biol.*, 13, 238 (1965), FR-2,315,991 and FR-2,416,008).

The cosmetic compositions according to the invention may be formulated for protecting the human epidermis or the hair against the damaging effects of ultraviolet radiation, as an anti-sun composition or as a makeup product.

When the cosmetic compositions according to the invention are formulated for protecting the human epidermis against UV rays, or as anti-sun/sunscreen compositions, same may be provided in the form of a suspension or a dispersion in solvents or fatty substances, in the form of a nonionic vesicular dispersion or, alternatively, in the form of an emulsion, such as a cream or a milk, in the form of an ointment, a gel, a gel cream, a solid stick, a powder, a stick, an aerosol foam or a spray.

When the cosmetic compositions according to the invention are formulated for protecting the hair against UV rays, same may be provided in the form of a shampoo, a lotion, a gel, an emulsion, a nonionic vesicular dispersion and may constitute, for example, a rinse-off composition to be applied before or after shampooing, before or after dyeing or bleaching, before, during or after permanent-waving or hair straightening, a hair-styling or treatment lotion or gel, a lotion or gel for blow drying or hair setting, a composition for permanent waving or straightening, dyeing or bleaching the hair.

When the subject compositions are formulated as makeup products for the eyelashes, the eyebrows or the skin, such as a treatment cream for the epidermis, foundation, lipstick, eyeshadow, blusher, mascara or eyeliner, same may be provided in a solid or pasty, anhydrous or aqueous form, nonionic vesicular dispersions or alternatively suspensions.

As indicated above, the present invention thus features formulating the subject emulsions for the production of cosmetic compositions for protecting the skin and/or the hair against ultraviolet radiation, in particular solar radiation.

This invention also features formulating non-UV-screening organomodified silicones as described above for the production of photoprotective cosmetic or dermatological water-in-oil. emulsions containing at least one organic UV-screening agent insoluble therein, for increasing the water resistance of its screening power (stability to water).

In order to further illustrate the present invention and the advantages thereof, the following specific formulation example is given, it being understood that same is intended only as illustrative and in nowise limitative.

EXAMPLE

| COMPOSITION W/O Emulsion | Weight in grams |
|---|---|
| Oxyethylenated polydimethyl/methylcetyl methylsiloxane (ABIL EM 90D - GOLDSCHMIDT) | 2 |
| Phenyl trimethylsiloxy trisiloxane (DOW CORNING 556 COSMETIC grade fluid - DOW CORNING) | 3 |
| $C_{12}/C_{15}$ alcohol benzoate (WITCONOL TN - WITCO) | 8 |
| Methylenebis(tetramethylbutylhydroxyphenylbenzo-triazole) in micronized form marketed under the trademark TINOSORB M Mean particle size 150 mn to 200 mn | 5 |
| Drometrizole Trisiloxane | 2 |
| 2,4-bis{[4-2-Ethythexyloxy)]-2-hydroxy]phenyl}-6-(4-methoxyphenyl)-1,3,5-triazine | 2 |
| Titanium dioxide (TITANIUM DIOXYDE MT-100 TV TAYCA) | 3 |
| Glycerin | 5 |
| Magnesium sulfate | 0.7 |
| Preservatives | qs |
| Demineralized water qs | 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, water-resistant UV-photoprotecting cosmetic/dermatological water-in-oil (W/O) emulsion comprising (a) at least one aqueous phase and (b) at least one fatty phase, (c) an effective UV-photoprotecting amount of at least one micronized organic UV-screening agent insoluble therein, the mean particle size of said micronized particles ranging from 0.01 to 2 µm, and (d) at least one oxyalkylenated non-UV-screening organomodified silicone.

2. The topically applicable UV-photoprotecting W/O emulsion as defined by claim 1, said at least one insoluble organic UV-screening agent neither being micronized 2,4,6-tris[p-2'-ethylhexyl-1'-oxycarbonyl)anilino]-1,3,5-triazine, nor the compound having the structural formula:

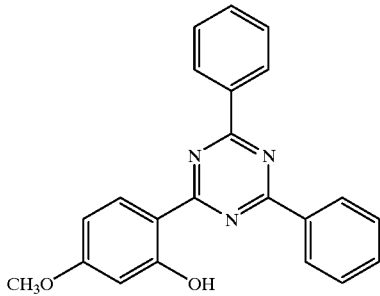

in micronized insoluble form.

3. The topically applicable UV-photoprotecting W/O emulsion as defined by claim 1, said at least one non-UV-screening organomodified silicone comprising an oil, a wax, a resin or a gum.

4. The topically applicable UV-photoprotecting W/O emulsion as defined by claim 1, said at least one non-UV-screening organomodified silicone comprising an oxyethylenated and/or oxypropylenated polyorganosiloxane.

5. The topically applicable UV-photoprotecting W/O emulsion as defined by claim 1, said at least one non-UV-screening organomodified silicone having the following structural formula (I):

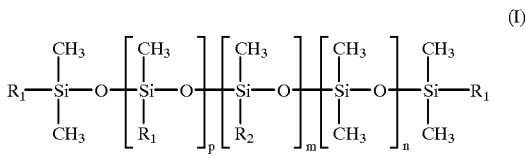

in which the radicals $R_1$, which may be identical or different, are each a linear or branched $C_1$–$C_{30}$ alkyl radical or a phenyl radical; the radicals $R_2$, which may be identical or different, are each a radical —$C_cH_{2c}$—(—O—$C_2H_4$)$_a$—(—O—$C_3H_6$)$_b$—(O—$C_4H_8$)$_d$—$R_3$ wherein the radicals $R_3$, which may be identical or different, are each a hydrogen atom, a hydroxyl radical, a linear or branched alkyl radical having from 1 to 12 carbon atoms, a linear or branched alkoxy radical having from 1 to 6 carbon atoms, a linear or branched acyloxy radical having from 2 to 12 carbon atoms, a radical —NHCH$_2$CH$_2$COOM, an aminoalkyl radical optionally substituted on the amine function, a $C_1$–$C_{30}$ carboxyacyl radical, an optionally substituted phosphono group, a radical —OCO—(CH$_2$)$_d$—CO$_2$M, —NHCO(CH$_2$)$_d$OH or —NH$_3$Y, the variables M, which may be identical or different, are each a hydrogen atom, Na, K, Li, NH$_4$ or an organic amine, Y is a monovalent inorganic or organic anion, a ranges from 0 to 100, b ranges from 0 to 50, c ranges from 0 to 5, a+b is greater than or equal to 1, d ranges from 0 to 10, m ranges from 0 to 20, n ranges from 0 to 500, p ranges from 0 to 50.

6. The topically applicable UV-photoprotecting W/O emulsion as defined by claim 4, wherein formula (I) the radicals $R_1$ are all methyl radicals and the radical $R_3$ is a hydroxyl group.

7. The topically applicable UV-photoprotecting W/O emulsion as defined by claim 6, said at least one non-UV-screening organomodified silicone of formula (I) comprising an oxyethylenated oxypropylenated polydimethyl/methyl siloxane (EO/PO 18/18) in which p+n is 396 and m is 4, (CTFA designation: cyclomethicone 90% dimethicone copolyol 10%).

8. The topically applicable UV-photoprotecting W/O emulsion as defined by claim 4, wherein formula (I) the radicals $R_1$ are methyl radicals or $C_2$–$C_{30}$ alkyl radicals and the radical $R_3$ is a hydroxyl group.

9. The topically applicable UV-photoprotecting W/O emulsion as defined by claim 4, said at least one non-UV-screening organomodified silicone of formula (I) comprising an oxyethylenated oxypropylenated polymethyllauryl/methyl siloxane (EO/PO 18/18) in which p+n is 35 and m is 3, (CTFA designation: laurylmethicone copolyol 91%, isostearyl alcohol 9%).

10. The topically applicable UV-photoprotecting W/O emulsion as defined by claim 4, said at least one non-UV-screening organomodified silicone of formula (I) comprising an oxyethylenated oxypropylenated polymethylcetyl/methyl siloxane, in which p is 20 to 25, m is 5 and n is 75 (CTFA designation: cetyldimethicone copolyol).

11. The topically applicable UV-photoprotecting W/O emulsion as defined by claim 1, said at least one non-UV-screening organomodified silicone comprising a linear α,ω-substituted oxyalkylenated silicone having oxyalkylenated endgroups bonded to Si atoms via hydrocarbon radicals.

12. The topically applicable UV-photoprotecting W/O emulsion as defined by claim 1, said at least one non-UV-screening organomodified silicone having the following structural formula (II):

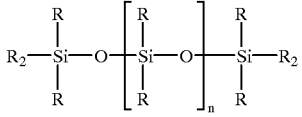

(II)

in which n ranges from 1 to 500; the radicals $R_2$, which may be identical or different, are each a radical $-C_cH_{2c}-(-O-C_2H_4)_a-(-O-C_3H_6)_b-(O-C_4H_8)_d-R_3$ wherein a, b, c and $R_3$ are defined as in formula (I) and the radicals R, which may be identical or different, are each a linear or branched $C_1-C_{30}$ alkyl radical or a phenyl radical.

13. The topically applicable UV-photoprotecting W/O emulsion as defined by claim 12, wherein formula (II) the radicals R are methyl radicals; c ranges from 2 to 4, a ranges from 3 to 100, b ranges from 1 to 50, d equals 0, $R_3$ is a hydroxyl group, and n ranges from 50 to 200.

14. The topically applicable UV-photoprotecting W/O emulsion as defined by claim 12, wherein the weight ratio of the $C_2H_4O$ units relative to the $C_3H_6O$ units ranges from 100:10 to 20:80.

15. The topically applicable UV-photoprotecting W/O emulsion as defined by claim 1, comprising from 0.1% to 20% by weight of said at least one non-UV-screening organomodified silicone.

16. The topically applicable UV-photoprotecting W/O emulsion as defined by claim 1, said at least one insoluble organic UV-screening agent comprising an oxanilide, triazine, triazole, vinylamide, or cinnamide.

17. The topically applicable UV-photoprotecting W/O emulsion as defined by claim 16, said at least one insoluble organic UV-screening agent comprising an oxanilide having the structural formula (1):

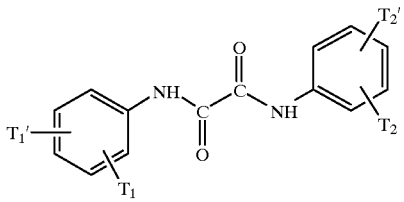

(1)

in which $T_1$, $T'_1$, $T_2$ and $T'_2$, which may be identical or different, are each a $C_1-C_8$ alkyl radical or a $C_1-C_8$ alkoxy radical.

18. The topically applicable UV-photoprotecting W/O emulsion as defined by claim 16, said at least one insoluble organic UV-screening agent comprising a triazine having the structural formula (2):

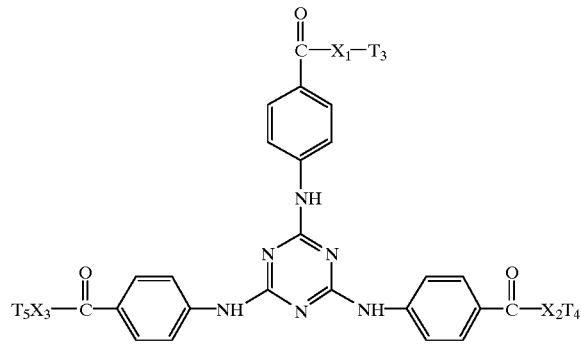

(2)

in which $X_1$, $X_2$ and $X_3$, which may be identical or different, are each an oxygen atom or a radical $-NZ-$; the radicals Z, which may be identical or different, are each hydrogen or a linear or branched $C_1-C_{18}$ alkyl radical, a $C_5-C_{12}$ cycloalkyl radical which may be substituted with one or more $C_1-C_4$ alkyl radicals; $T_3$, $T_4$ and $T_5$, which may be identical or different, are each hydrogen, an alkali metal, an ammonium radical which is optionally substituted with one or more alkyl or hydroxyalkyl radicals, a linear or branched $C_1-C_{18}$ alkyl radical, a $C_5-C_{12}$ cycloalkyl radical which is optionally substituted with one or more $C_1-C_4$ alkyl radicals, a polyoxyethylenated radical containing from 1 to 6 ethylene oxide units and whose terminal OH group is methylated, or a radical of the following formula (3), (4) or (5):

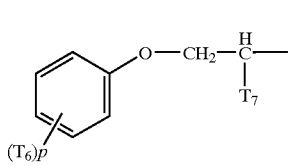

(3)

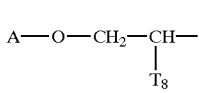

(4)

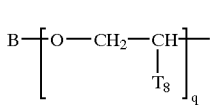

(5)

wherein $T_6$ is hydrogen or a methyl radical; $T_7$ is a $C_1-C_9$ alkyl radical; p is an integer ranging from 0 to 3; q is an integer ranging from 1 to 10; A is a $C_4-C_8$ alkyl radical or a $C_5-C_8$ cycloalkyl radical; B is a linear or branched $C_1-C_8$ alkyl radical, a $C_1-C_8$ cycloalkyl radical, or an aryl radical which is optionally substituted with one or more $C_1-C_4$ alkyl radicals; and $T_8$ is hydrogen or a methyl radical.

19. The topically applicable UV-photoprotecting W/O emulsion as defined by claim 18, said triazine UV-screening agent having the following structural formula:

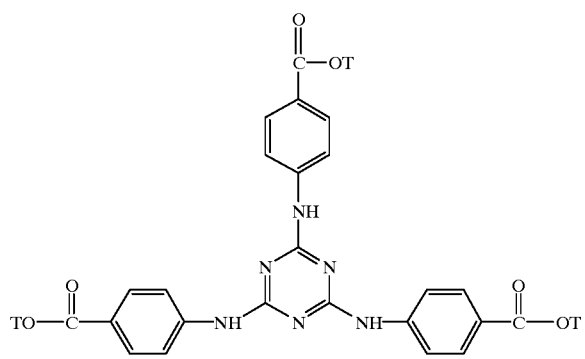

in which T is a 2-ethylhexyl radical.

20. The topically applicable UV-photoprotecting W/O emulsion as defined by claim 18, said triazine UV-screening agent having the following structural formula:

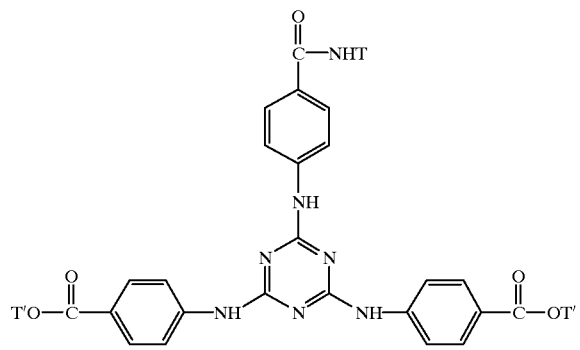

in which T' is a 2-ethylhexyl radical and T is a tert-butyl radical.

21. The topically applicable UV-photoprotecting W/O emulsion as defined by claim 16, said at least one organic UV-screening agent comprising an insoluble s-triazine bearing benzalmalonate and/or phenylcyanoacrylate substituents.

22. The topically applicable UV-photoprotecting W/O emulsion as defined by claim 21, said at least one triazine UV-screening agent comprising 2,4,6-tris(diethyl 4'-aminobenzalmalonate)-s-triazine; 2,4,6-tris(diisopropyl 4'-aminobenzalmalonate)-s-triazine; 2,4,6-tris(dimethyl 4'-aminobenzalmalonate)-s-triazine or 2,4,6-tris(ethyl α-cyano-4-aminocinnamate)-s-triazine.

23. The topically applicable UV-photoprotecting W/O emulsion as defined by claim 16, said at least one insoluble organic UV-screening agent comprising a triazine having the following structural formula:

(6)

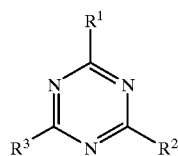

in which $R^1$, $R^2$, $R^3$ are independently phenyl, phenoxy, or pyrrolo radicals, optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a meth- ylidenecamphor group, a radical —(CH=CH)$_n$(CO)—OR$^4$, wherein $R^4$ is $C_1$–$C_{18}$ alkyl or cinnamyl, and n is equal to 0 or 1.

24. The topically applicable UV-photoprotecting W/O emulsion as defined by claim 16, said at least one organic UV-screening agent comprising an s-triazine bearing benzotriazole and/or benzothiazole substituents.

25. The topically applicable UV-photoprotecting W/O emulsion as defined by claim 24, said at least one insoluble triazine UV-screening agent comprising 2,4,6-tris [(3'-benzotriazol-2-yl-2'-hydroxy-5'-methyl)phenylamino]-s-triazine, or 2,4,6-tris[(3'-benzotriazol-2-yl-2'-hydroxy-5'-ter-octyl)phenylamino]-s-triazine.

26. The topically applicable UV-photoprotecting W/O emulsion as defined by claim 16, said at least one insoluble organic UV-screening agent comprising a triazole having the following structural formula (7):

(7)

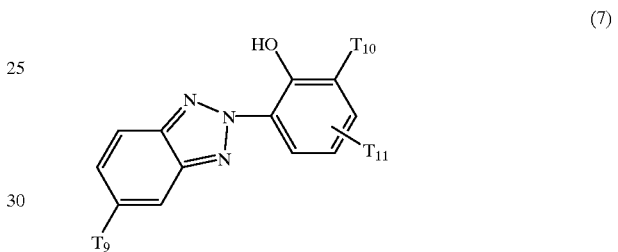

in which $T_9$ is a hydrogen atom or a $C_1$–$C_{18}$ alkyl radical; and $T_{10}$ and $T_{11}$, which may be identical or different, are each a $C_1$–$C_{18}$ alkyl radical which is optionally substituted with a phenyl radical.

27. The topically applicable UV-photoprotecting W/O emulsion as defined by claim 26, said compound of formula (7) being selected from among:

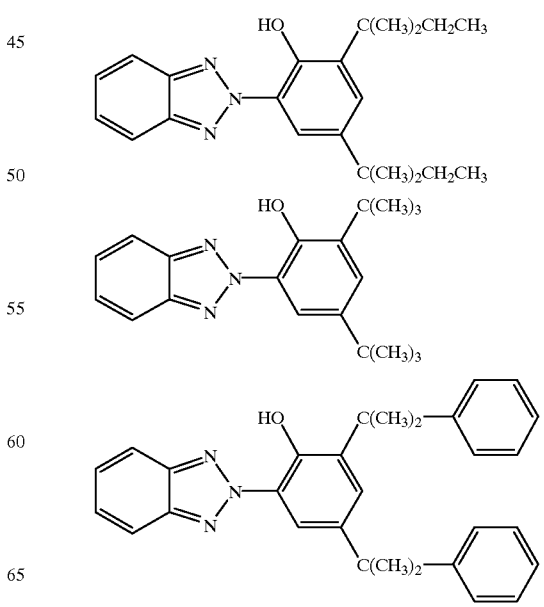

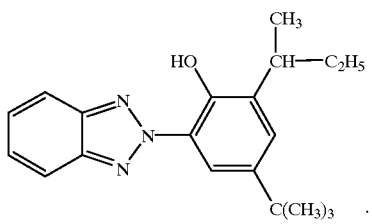

28. The topically applicable UV-photoprotecting W/O emulsion as defined by claim 16, said at least one insoluble organic UV-screening agent comprising [2,4'-dihydroxy-3-(2H-benzotriazol-2-yl)-5-(1,1,3,3-tetramethylbutyl)-2'-n-octoxy-5'-benzoyl]diphenylmethane having the structural formula:

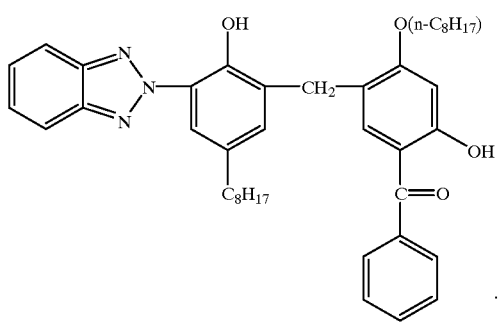

29. The topically applicable UV-photoprotecting W/O emulsion as defined by claim 16, said at least one insoluble organic UV-screening agent comprising a methylenebis(hydroxyphenylbenzo-triazole) having the following structural formula:

(8)

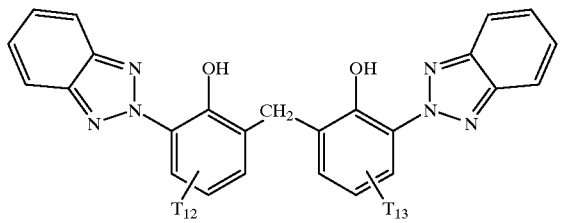

in which the radicals $T_{12}$ and $T_{13}$, which may be identical or different, are each a $C_1$–$C_{18}$ alkyl radical optionally substituted with one or more $C_1$–$C_4$ alkyl, $C_1$–$C_{12}$ cycloalkyl, or aryl radicals.

30. The topically applicable UV-photoprotecting W/O emulsion as defined by claim 29, said compound of formula (8) being selected from among:

compound (a)

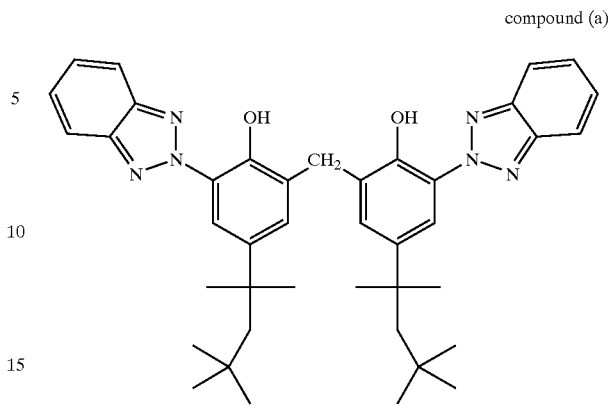

compound (b)

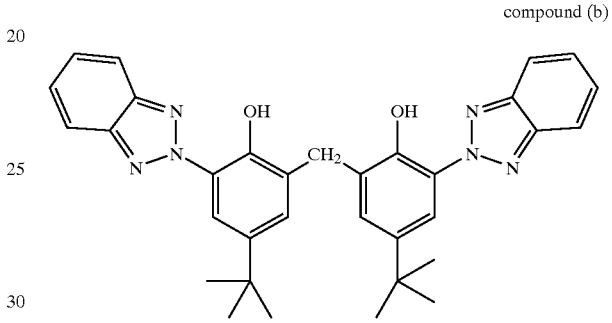

compound (c)

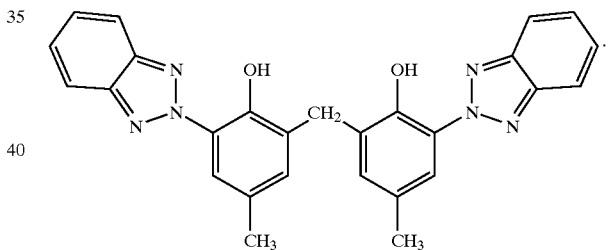

31. The topically applicable UV-photoprotecting W/O emulsion as defined by claim 16, said at least one insoluble organic UV-screening agent comprising a vinylamide having the following structural formula:

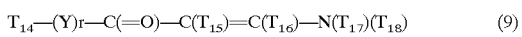

(9)

in which $T_{14}$ is a $C_1$–$C_{18}$ alkyl radical or a phenyl radical which is optionally substituted with one, two or three radicals selected from among OH, $C_1$–$C_{18}$ alkyl, $C_1$–$C_8$ alkoxy, or a radical —C(=O)—$OT_{19}$ wherein $T_{19}$ is a $C_1$–$C_{18}$ alkyl radical; $T_{15}$, $T_{16}$, $T_{17}$ and $T_{18}$, which may be identical or different, are each a $C_1$–$C_{18}$ alkyl radical or a hydrogen atom; Y is N or O and r is equal to 0 or 1.

32. The topically applicable UV-photoprotecting W/O emulsion as defined by claim 31, said compound of formula (9) comprising 4-octylamino-3-penten-2-one; ethyl 3-octylamino-2-butenoate; 3-octylamino-1-phenyl-2-buten-1-one; or 3-dodecylamino-1-phenyl-2-buten-1-one.

33. The topically applicable UV-photoprotecting W/O emulsion as defined by claim 16, said at least one insoluble organic UV-screening agent comprising a cinnamamide having the following structural formula:

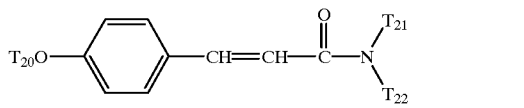

(10)

in which $OT_{20}$ is a hydroxyl or $C_1$–$C_4$ alkoxy radical; $T_{21}$ is hydrogen or $C_1$–$C_4$ alkyl; $T_{22}$ is a radical —(CONH)s-phenyl wherein s is equal to 0 or 1 and the phenyl group may be substituted with one, two or three groups selected from among OH, $C_1$–$C_{18}$ alkyl, $C_1$–$C_8$ alkoxy, or a radical —C(=O)—$OT_{23}$ wherein $T_{23}$ is a $C_1$–$C_{18}$ alkyl, phenyl, 4-methoxyphenyl or phenylaminocarbonyl group.

34. The topically applicable UV-photoprotecting W/O emulsion as defined by claim 16, said at least one insoluble organic UV-screening agent comprising a cinnamamide dimer.

35. The topically applicable UV-photoprotecting W/O emulsion as defined by claim 34, said insoluble organic UV-screening agent having the structural formula:

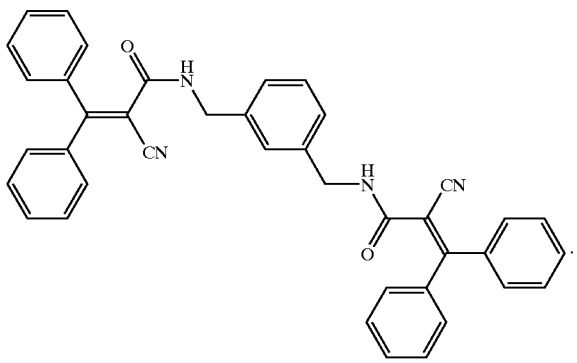

36. The topically applicable UV-photoprotecting W/O emulsion as defined by claim 1, said at least one insoluble organic UV-screening agent comprising a polyvalent metal salt of a sulfonic or carboxylic organic screening agent.

37. The topically applicable UV-photoprotecting W/O emulsion as defined by claim 36, said at least one insoluble organic UV-screening agent comprising a polyvalent metal salt of a sulfonated derivative of benzylidenecamphor, a polyvalent metal salt of a sulfonated derivative of benzimidazole, or a polyvalent metal salt of a derivative of cinnamic acid.

38. The topically applicable UV-photoprotecting W/O emulsion as defined by claim 1, said at least one insoluble organic UV-screening agent comprising a complex of a polyvalent metal or of ammonium with organic UV-A and/or UV-B screening agents.

39. The topically applicable UV-photoprotecting W/O emulsion as defined by claim 1, the mean particle size of said micronized particles ranging from 0.02 to 1.5 μm.

40. The topically applicable UV-photoprotecting W/O emulsion as defined by claim 39, the mean particle size of said micronized particles ranging from 0.03 to 1.0 μm.

41. The topically applicable UV-photoprotecting W/O emulsion as defined by claim 1, said micronized particles having been formed by grinding course particulates of said insoluble organic UV-screening agent in the presence of a surfactant.

42. The topically applicable UV-photoprotecting W/O emulsion as defined by claim 41, said surfactant comprising an alkyl polyglucoside having the formula $C_nH_{2n+1}O$ $(C_6H_{10}O_5)_xH$ in which n is an integer ranging from 8 to 16 and x is the average degree of polymerization of the structural unit ($C_6H_{10}O_5$) and varies from 1.4 to 1.6.

43. The topically applicable UV-photoprotecting W/O emulsion as defined by claim 41, said surfactant being present at a concentration ranging from 1% to 50% by weight relative to the insoluble organic UV-screening agent in its micronized state.

44. The topically applicable UV-photoprotecting W/O emulsion as defined by claim 1, formulated into a cosmetically/dermatologically acceptable vehicle, diluent or carrier therefor.

45. The topically applicable UV-photoprotecting W/O emulsion as defined by claim 1, further comprising one or more additional organic screening agents active in UV-A and/or UV-B range, soluble in one of the phases thereof.

46. The topically applicable UV-photoprotecting W/O emulsion as defined by claim 45, said one or more additional organic screening agents being selected from among cinnamic derivatives; salicylic derivatives; camphor derivatives; triazine derivatives; dibenzoyl-methane derivatives; benzophenone derivatives; β, β'-diphenyl acrylate derivatives; benzimidazole derivatives; dimers of α-alkylstyrene; bisbenzoazolyl derivatives; p-aminobenzoic acid derivatives; polymer screening agents and silicone screening agents.

47. The topically applicable UV-photoprotecting W/O emulsion as defined by claim 1, further comprising coated or uncoated pigments or nanopigments of metal oxides.

48. The topically applicable UV-photoprotecting W/O emulsion as defined by claim 47, further comprising pigments or nanopigments of titanium, zinc, iron, zirconium or cerium oxides, or mixtures thereof.

49. The topically applicable UV-photoprotecting W/O emulsion as defined by claim 1, further comprising at least one agent for tanning and/or for artificial tanning of the skin.

50. The topically applicable UV-photoprotecting W/O emulsion as defined by claim 1, further comprising at least one fatty substance, organic solvent, thickener, demulcent, opacifier, stabilizer, emollient, anti-foaming agent, moisturizing agent, perfume, preservative, colorant, polymer, filler, sequestrant, propellant, alkalinizing or acidifying agent, or combination thereof.

51. The topically applicable UV-photoprotecting W/O emulsion as defined by claim 1, formulated as a nonionic vesicular dispersion, a cream, a milk, a gel, a lotion, an ointment, a gel cream, a suspension, a dispersion, a powder, a shampoo, a solid stick, a foam or a spray.

52. The topically applicable UV-photoprotecting W/O emulsion as defined by claim 1, formulated as a makeup composition for the eyelashes, the eyebrows or the skin and being in solid or pasty, anhydrous or aqueous form, or in the form of a suspension or a dispersion.

53. A method or regime/regimen for photoprotecting human skin and/or hair against the deleterious effects of ultraviolet radiation, comprising topically applying thereto an effective amount of the UV-photoprotecting cosmetic/dermatological W/O emulsion as defined by claim 1.

54. A method or regime/regimen for photoprotecting human skin and/or hair against the deleterious effects of solar radiation, comprising topically applying thereto an effective amount of the UV-photoprotecting cosmetic/dermatological W/O emulsion as defined by claim 1.

* * * * *